(12) United States Patent
Noble et al.

(10) Patent No.: US 7,383,728 B2
(45) Date of Patent: Jun. 10, 2008

(54) ORIENTATION AND MOTION SENSING IN ATHLETIC TRAINING SYSTEMS, PHYSICAL REHABILITATION AND EVALUATION SYSTEMS, AND HAND-HELD DEVICES

(75) Inventors: Christopher R. Noble, Winchester, MA (US); Kenneth S. Lyons, Middleboro, MA (US)

(73) Assignee: Ultimate Balance, Inc., Winchester, MA (US)

( * ) Notice: Subject to any disclaimer, the term of this patent is extended or adjusted under 35 U.S.C. 154(b) by 42 days.

(21) Appl. No.: 11/485,180

(22) Filed: Jul. 12, 2006

(65) Prior Publication Data

US 2007/0015611 A1 Jan. 18, 2007

Related U.S. Application Data

(60) Provisional application No. 60/719,161, filed on Sep. 21, 2005, provisional application No. 60/698,995, filed on Jul. 13, 2005.

(51) Int. Cl.
*A61B 5/22* (2006.01)
(52) U.S. Cl. .................... 73/379.01; 600/595
(58) Field of Classification Search ............. 73/379.01, 73/397.02; 600/595
See application file for complete search history.

(56) References Cited

U.S. PATENT DOCUMENTS

| | | | |
|---|---|---|---|
| 1,169,188 A | 1/1916 | Peck | |
| 3,945,646 A | 3/1976 | Hammond | |
| 4,502,035 A | 2/1985 | Obenauf et al. | 340/323 |
| 4,991,850 A | 2/1991 | Wilhlem | |
| 5,197,489 A | 3/1993 | Conlan | |
| 5,221,088 A | 6/1993 | McTeigue et al. | 273/187.2 |
| 5,243,998 A | 9/1993 | Silverman et al. | |
| 5,251,902 A | 10/1993 | Federowicz et al. | 273/187.2 |
| 5,253,870 A | 10/1993 | Bedney | 273/187.2 |
| 5,338,036 A | 8/1994 | Takeuchi et al. | 273/187.2 |
| 5,348,519 A | 9/1994 | Prince et al. | |
| 5,372,365 A * | 12/1994 | McTeigue et al. | 473/409 |
| 5,373,857 A | 12/1994 | Travers et al. | |

(Continued)

FOREIGN PATENT DOCUMENTS

WO   WO 95/32666   12/1995

(Continued)

*Primary Examiner*—Jewel V Thompson
(74) *Attorney, Agent, or Firm*—Weingarten, Schurgin, Gagnebin & Lebovici LLP

(57) ABSTRACT

Improved apparatus and methods of sensing or monitoring body orientation and motion and measuring range of motion (ROM) for use in athletic training and physical rehabilitation and evaluation. The apparatus includes a 3-axis sensor, at least one memory, and at least one processor, and is attachable to an object to be monitored. The 3-axis sensor senses a magnitude of tilt along each of a first, second, and third axis, the memory stores data representing the sensed magnitudes of tilt, and the processor processes the data stored in the memory. In one embodiment, the processor determines an angle between each of the first, second, and third axes and a horizontal plane, and selects the two axes corresponding to the two smallest angles between the three axes and the horizontal plane. The processor then generates an indication of the orientation of the object based upon the sensed magnitudes of tilt along the two selected axes.

45 Claims, 10 Drawing Sheets

U.S. PATENT DOCUMENTS

| | | | |
|---|---|---|---|
| 5,430,435 A | 7/1995 | Hoch et al. | |
| 5,524,894 A | 6/1996 | Shannon | 473/209 |
| 5,553,857 A | 9/1996 | Fish | 473/209 |
| 5,592,401 A | 1/1997 | Kramer | |
| 5,621,922 A | 4/1997 | Rush, III | |
| 5,836,829 A | 11/1998 | Van Cott et al. | |
| 5,891,180 A | 4/1999 | Greeninger et al. | |
| 5,895,328 A | 4/1999 | Pahio | |
| 5,913,727 A | 6/1999 | Ahdoot | |
| 5,916,181 A | 6/1999 | Socci et al. | 600/595 |
| 5,993,323 A | 11/1999 | Linenfelser | 473/209 |
| 6,032,530 A | 3/2000 | Hock | 73/379.01 |
| 6,038,074 A * | 3/2000 | Kitaguchi et al. | 359/618 |
| 6,048,324 A | 4/2000 | Socci et al. | 600/595 |
| 6,059,576 A | 5/2000 | Brann | |
| 6,196,932 B1 | 3/2001 | Marsh et al. | |
| 6,307,481 B1 | 10/2001 | Lehrman et al. | 340/669 |
| 6,331,168 B1 | 12/2001 | Socci et al. | |
| 6,334,837 B1 | 1/2002 | Hein et al. | |
| 6,546,291 B2 | 4/2003 | Merfeld et al. | |
| 6,568,396 B1 | 5/2003 | Anthony | |
| 6,582,380 B2 | 6/2003 | Kazlausky et al. | |
| 6,611,783 B2 | 8/2003 | Kelly, Jr. et al. | 702/150 |
| 6,678,549 B2 | 1/2004 | Cusimano et al. | |
| 6,730,047 B2 * | 5/2004 | Socci et al. | 600/595 |
| 6,836,971 B1 | 1/2005 | Wan | |
| 6,871,413 B1 | 3/2005 | Arms et al. | 33/366.11 |
| 2001/0032059 A1 | 10/2001 | Kelly, Jr. et al. | 702/150 |
| 2002/0060633 A1 | 5/2002 | Crisco, III et al. | |
| 2002/0077189 A1 | 6/2002 | Tuer et al. | |
| 2002/0077570 A1 | 6/2002 | McLeod et al. | |
| 2002/0116147 A1 | 8/2002 | Vock et al. | |
| 2002/0123386 A1 | 9/2002 | Perlmutter | |
| 2002/0134153 A1 | 9/2002 | Grenlund | |
| 2002/0173364 A1 | 11/2002 | Boscha | |
| 2002/0173365 A1 | 11/2002 | Boscha | |
| 2002/0183657 A1 * | 12/2002 | Socci et al. | 600/595 |
| 2002/0187860 A1 | 12/2002 | Shoane | |
| 2003/0028377 A1 | 2/2003 | Noyes | |
| 2003/0116166 A1 | 6/2003 | Anthony | |
| 2003/0135129 A1 | 7/2003 | Cusimano et al. | |
| 2003/0138763 A1 | 7/2003 | Roncalez et al. | |
| 2003/0144088 A1 | 7/2003 | Shoane | |
| 2003/0163287 A1 | 8/2003 | Vock et al. | |
| 2003/0207718 A1 | 11/2003 | Perlmutter | |
| 2003/0216228 A1 | 11/2003 | Rast | |
| 2004/0001373 A1 | 1/2004 | Liaw et al. | |
| 2004/0006747 A1 | 1/2004 | Tyler | |
| 2004/0008427 A1 | 1/2004 | Nattermann et al. | |
| 2004/0010390 A1 | 1/2004 | Kelly, Jr. et al. | 702/150 |
| 2004/0014531 A1 | 1/2004 | Ziener-Gundersen | |
| 2004/0033843 A1 * | 2/2004 | Miller et al. | 473/274 |
| 2004/0077438 A1 | 4/2004 | Choi | |
| 2004/0259651 A1 | 12/2004 | Storek | |
| 2005/0288119 A1 * | 12/2005 | Wang et al. | 473/223 |
| 2006/0284979 A1 * | 12/2006 | Clarkson | 348/143 |
| 2007/0124075 A1 * | 5/2007 | Lee et al. | 701/220 |

FOREIGN PATENT DOCUMENTS

| | | |
|---|---|---|
| WO | WO 98/24242 | 6/1998 |
| WO | WO 99/18657 | 4/1999 |
| WO | WO 99/21477 | 5/1999 |
| WO | WO 99/26704 | 6/1999 |
| WO | WO 00/17615 | 3/2000 |
| WO | WO 01/50957 | 7/2001 |
| WO | WO 01/66006 | 9/2001 |
| WO | WO 02/076293 | 10/2002 |
| WO | WO 02/093272 | 11/2002 |
| WO | WO 02/102475 | 12/2002 |
| WO | WO 03/029745 | 4/2003 |
| WO | WO 03/061779 | 7/2003 |
| WO | WO 03/068339 | 8/2003 |
| WO | WO 2004/008427 | 1/2004 |

* cited by examiner

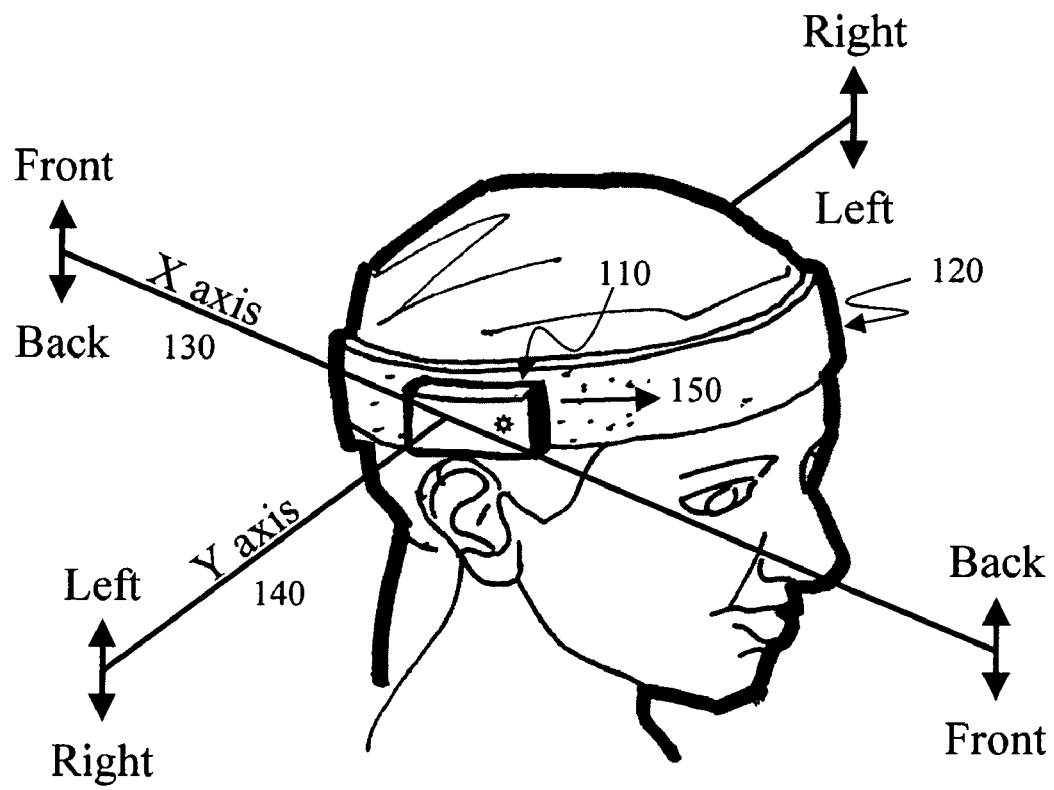
Figure 1 – Prior Art

ORIENTATION AND MOTION SENSING IN ATHLETIC TRAINING SYSTEMS, PHYSICAL REHABILITATION AND EVALUATION SYSTEMS, AND HAND-HELD DEVICES

CROSS REFERENCE TO RELATED APPLICATIONS

This application claims benefit of U.S. Provisional Patent Application No. 60/698,995 filed Jul. 13, 2005 entitled MONITORING, EVALUATION AND TRAINING SYSTEM FOR ATHLETICS AND PHYSICAL REHABILITATION INCLUDING STUDENT UNIT AND REMOTE UNIT COMMUNICABLE THEREWITH, and U.S. Provisional Patent Application No. 60/719,161 filed Sep. 21, 2005 entitled MONITORING, EVALUATION AND TRAINING SYSTEM FOR ATHLETICS AND PHYSICAL REHABILITATION INCLUDING STUDENT UNIT AND REMOTE UNIT COMMUNICABLE THEREWITH.

STATEMENT REGARDING FEDERALLY SPONSORED RESEARCH OR DEVELOPMENT

Not applicable

BACKGROUND OF THE INVENTION

The present invention relates generally to the fields of athletic training, physical rehabilitation and evaluation, and physical activity monitoring, and more specifically to apparatus and methods of monitoring the orientation of body parts, measuring the range of motion of joints or limbs of the body, measuring levels of physical activity, and providing cuing and measurement feedback for training and rehabilitation purposes. The present invention also relates to hand-held devices for sensing the orientation and motion of body parts or other objects.

Athletic training systems and apparatus are known that may be employed to monitor the orientation or movement of a user's body as he or she engages in a particular sporting activity. For example, a conventional athletic training system may be attached to the user's head or any other suitable body part, and may include a number of tilt sensors for detecting the direction of tilt of the user's head relative to a user reference orientation (such as a "straight ahead" reference orientation) and/or to an adjustable tilt threshold magnitude. Such a conventional system may provide the user with one or more visible or audible indications of the orientation or movement of his or her body in real time. The user may employ the system to train his or her body to maintain a desired body posture or to execute a desired movement while performing a particular sporting activity. In addition, patients receiving physical therapy for balance disorders or other posture-related conditions may use the system to monitor their progress while performing rehabilitation exercises, or to monitor their posture as they go about their daily activities.

Although athletic training systems like the conventional system described above may be employed in various sporting and physical therapy applications, such systems have drawbacks. For example, in some conventional athletic training systems, the tilt sensors include accelerometers, which, because accelerometers are responsive to both acceleration and tilt, can generate misleading signals when the body part is accelerating. Further, when an accelerometer is used as a tilt sensor, the sensitivity and accuracy of the accelerometer are generally high when the sensitive axis of the accelerometer is close to horizontal, i.e., parallel to the earth's surface, but typically worsen as the sensitive axis of the accelerometer becomes vertical, i.e., perpendicular to the earth's surface. Moreover, it is often desirable to mount such athletic training systems in various orientations and/or on different parts of the user's body to suit a particular application and/or for aesthetic reasons. However, conventional athletic training systems typically require the sensitive axes of the tilt sensors to be precisely aligned relative to corresponding axes of the user. For example, when the system is attached to the user's headband, baseball helmet, or golf cap, the sensitive axis of one tilt sensor may have to be precisely aligned with the left/right axis of the user's head, while the sensitive axis of another tilt sensor may have to be precisely aligned with the front/back axis of the user's head. In addition, some users of conventional athletic training systems may be incapable of recognizing or responding to the visible or audible indications provided by the system. Alternatively, the type of visible or audible feedback provided by the conventional system may be insufficient in some applications, e.g., when an attending therapist requires quantitative feedback relating to the user's balance skill level, range of motion, conformance to a requested motion or sequence of motions, and/or in applications where users may require guidance or instruction from the training system itself in the absence of the trainer or therapist. The visible or audible feedback may also be inappropriate or unduly distracting to others, e.g., when the system is used in public places.

Athletic training systems are also known that employ tilt sensors in combination with one or more angular rate sensors such as gyroscopes for sensing and analyzing sequences of movement rather than just monitoring orientation. However, in addition to the drawbacks of conventional athletic training systems listed above, angular rate sensors can be more expensive and larger than accelerometers, can consume more power, and can exhibit significant drift errors.

Athletic training systems are also known that employ techniques to "arm" the system, i.e., to initiate monitoring activity based upon an analysis of user movement. To initiate the monitoring activity, they typically require the user to maintain a steady position for a specified time-period, which can lead to errors because the user can sometimes remain motionless with no intention of initiating the monitoring activity.

A number of systems for measuring the range of motion (ROM) of a body part about a joint or limb of the user's body are also known. For example, one such system that may be employed in physical rehabilitation applications includes a pair of accelerometers to compensate for the reduction in sensitivity and accuracy than can occur as the sensitive axis of a single accelerometer becomes vertical. The pair of accelerometers of this system needs to be aligned with the intended axis of rotation of the measured body part. In addition, to reduce the generation of erroneous or misleading signals when detecting the tilt of a body part that is undergoing acceleration, the system monitors the outputs of each accelerometer for either a varying signal or an over-range signal, which can be indicative of such acceleration.

However, the above-described conventional system for measuring range of motion also has drawbacks. For example, the acceleration of a body part can cause a distortion in the sensor reading that is not characterized by an over-range or varying signal output, and the system may be incapable of detecting such a condition. Further, the system must typically be manipulated while the measurements are being taken, for example, to trigger a reading when determining the initial orientation or maximum extension during range of motion (ROM) measurements. Moreover, the system must typically be repositioned to perform multiple measurements on a single joint to re-establish precise alignment of the sensors with each new axis of motion. As a result, it can be difficult to establish and/or maintain a precise alignment of the system with an axis and/or fulcrum of a joint or bone. Such alignment and re-alignment of the system may also interfere with or slow down the measurement process, thereby making the measurement process inaccurate, or painful for the user. In addition, when this system is used for diagnostic or physical rehabilitation purposes, the measurement process may interfere with the visual and/or tactile communication between a physical therapist and his or her patient, and/or an additional attendant may be required to take the actual measurement readings.

Another known system for monitoring physical activity may be employed in pedometers and other activity-monitoring devices. In such a system, the primary objective is to measure accurately the magnitude of an oscillating acceleration, such as an up-down acceleration of a runner or a front-back acceleration of a rower, which is subsequently used to estimate activity level and/or for other purposes. The system includes a plurality of accelerometers disposed in different directions. Signals generated by the accelerometers are compared, and, in response to the signal comparison, one of the accelerometers is selected as being aligned closest to the direction of user acceleration of interest. However, this system has drawbacks in that there is a practical limit to the number of accelerometers that may be employed in the system. Further, the likelihood that any one of the accelerometers will be oriented precisely in the direction of user acceleration may be low.

A number of hand-held devices for sensing motion are also known. For example, one such hand-held device includes a 2-axis accelerometer operative to control the position a graphical pointer on a display screen. To reduce undesirable pointer movements when responding to the tilt of the accelerometer as it also undergoes acceleration, the device filters out the DC and low frequency components of the accelerometer output, and inserts a new DC component in the system output with a slow feedback loop to maintain correspondence between the average tilt of the accelerometer and the center of the screen. One drawback of this device is that it does not provide a measurement of the actual magnitude of the accelerometer output. In addition, this device fails to address the reduction in sensitivity and accuracy than can occur as the sensitive axis of the accelerometer becomes vertical.

It would therefore be desirable to have improved apparatus and methods of sensing or monitoring body orientation and motion and measuring range of motion (ROM), for use in athletic training, physical rehabilitation and evaluation, and any other suitable physical activity or exercise. Such improved apparatus for sensing orientation and motion would avoid the drawbacks of the above-described conventional systems and apparatus. It would also be desirable to have an improved method of sensing orientation and motion that can be used in hand-held devices.

BRIEF SUMMARY OF THE INVENTION

In accordance with the present invention, improved apparatus and methods of sensing or monitoring body orientation and motion and measuring range of motion (ROM) are disclosed, for use in athletic training, physical rehabilitation and evaluation, and any other suitable physical activity or exercise. In one embodiment of the present invention, an apparatus for monitoring the orientation of an object in 3-dimensional space is provided, including a 3-axis sensor, a least one memory, and at least one processor. The apparatus is configured to be attached to, mounted to, held against, or otherwise disposed in contact with the object to be monitored. The 3-axis sensor is configured to sense a magnitude of tilt along each of a first axis, a second axis, and a third axis, the memory is operative to store data representing the sensed magnitude of tilt along each of the three axes, and the processor is operative to process the data stored in the memory. Specifically, the processor determines an angle between each of the first, second, and third axes and the horizontal plane, and selects the two axes with the two smallest such angles. The processor then generates an indication of the orientation of the object based upon the sensed magnitude of tilt along the two selected axes. In this way, the apparatus provides increased sensitivity and accuracy in substantially any orientation relative to the object to which it is attached, even when one of the sensitive axes of the 3-axis sensor becomes vertical.

This first embodiment of the present invention may also be employed to detect the presence of acceleration. Specifically, the apparatus is attached to, mounted to, or held against the object to be monitored. Next, the apparent gravity force acting on the apparatus is measured. Next, the direction of the actual gravity force is determined by analyzing the variation in the apparent gravity force. A first vector representing the actual gravity force is then subtracted from a second vector representing the apparent gravity force to obtain a third vector representing the acceleration of the object. Next, an indication of the direction and/or the magnitude of the third vector is generated, thereby providing an indication of the acceleration of the object.

Another embodiment of the present invention may be employed in athletic training or any other suitable physical activity or exercise to determine a reference orientation of a user. The direction of tilt of a body part of the user can then be determined relative to the user's reference orientation, independently of the mounted orientation of the sensing apparatus. This embodiment of the present invention may be employed, for example, to monitor the direction and magnitude of tilt of the user's head while he or she plays tennis or golf. Specifically, the user's body part is positioned in a first orientation, and an apparent gravity force acting on the body part is measured to obtain a first direction of the apparent gravity force. Next, the body part undergoes an angular displacement about at least one axis from the first orientation to a second orientation, and the apparent gravity force acting on the body part is measured again to obtain a second direction of the apparent gravity force. The reference orientation of the user is then determined based upon the first and second directions of the apparent gravity force, and stored in memory. Because the user's reference orientation is stored in memory, directions of subsequent angular displacements of the body part can be determined relative to the stored reference orientation.

Still another embodiment of the present invention may be employed in physical rehabilitation and evaluation applications. For example, this embodiment of the present invention may be employed to measure the extension of a body part around a fixed joint fulcrum. First, a housing including a sensor is disposed against the body part. Next, the body part is positioned in a first orientation relative to the joint. The sensor then measures an apparent gravity force acting on the housing disposed against the body part to obtain a first direction of the apparent gravity force. Next, the body part is positioned in a second orientation relative to the joint. The sensor then measures the apparent gravity force acting on the housing at the second orientation to obtain a second direction of the apparent gravity force. A magnitude of rotation of the body part from the first orientation to the second orientation can then be determined based upon the first and second directions of the apparent gravity force, independent of the alignment between the body part and the housing.

In yet another embodiment of the present invention, the monitoring of the orientation of a body part can be initiated by a specified sequence of user motions, thereby obviating the need to manipulate the orientation and motion-sensing apparatus directly. In this embodiment, a sensor is disposed against the body part. Next, the body part is positioned in a first orientation, and the sensor is operated to provide data representing a first position of the body part. The body part is then positioned in at least one second orientation, and the sensor is operated to provide data representing at least one second position of the body part. If the first and second positions of the body part correspond to a specified sequence of user positions, then monitoring of the orientation of the body part by the sensor is initiated.

In another embodiment of the presently disclosed invention, useful feedback is provided to a user based upon the direction and/or extent of one or more rotations of a body part to which it is attached. In this embodiment, the apparatus includes a sensor, at least one memory, at least one processor, and an audio output system. The sensor is configured to sense an angular orientation of the body part, and to provide data representing the sensed angular orientation. The memory is operative to store data representing a plurality of words or phrases, and the audio output system generates an audible message in response to an electronic input. The processor monitors the data provided by the sensor, and accesses data stored in the memory corresponding to at least one word or phrase relating to the sensed angular orientation of the body part. In cooperation with the audio output system, the processor generates a message audible to the user that corresponds to the accessed word or phrase. For example, the word or phrase may include at least one instructional word or phrase for the user, or a confirmation of the start or completion of a specified act performed by the user or the apparatus during the course of monitoring the orientation of the body part. In alternative embodiments, the orientation and motion-sensing apparatus may provide feedback to the user in the form of one or more visible and/or tactile outputs.

Other features, functions, and aspects of the invention will be evident from the Detailed Description of the Invention that follows.

BRIEF DESCRIPTION OF THE SEVERAL VIEWS OF THE DRAWINGS

The invention will be more fully understood with reference to the following Detailed Description of the Invention in conjunction with the drawings of which:

FIG. 1 illustrates a conventional orientation and motion-sensing device attached to the head of a user;

FIG. 2b-2e depict a back end view, a back side view, a top view, and a front side view, respectively, of the device of FIG. 2a;

FIG. 4 is a block diagram of the device of FIG. 2a;

FIG. 5 is a diagram of a geometric model illustrating the operation of the device of FIG. 2a;

FIG. 9b is a schematic diagram illustrating a technique for discriminating between the tilt and motion stimuli of FIG. 9a.

DETAILED DESCRIPTION OF THE INVENTION

Figure 2A:
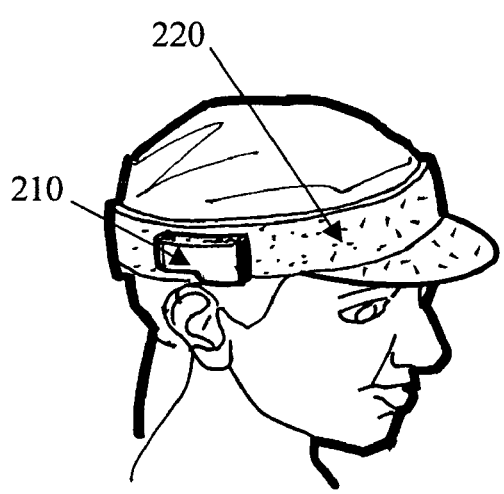
FIG. 2a illustrates an orientation and motion-sensing device according to the present invention.

The disclosures of U.S. Provisional Patent Application No. 60/698,995 filed Jul. 13, 2005 entitled MONITORING, EVALUATION AND TRAINING SYSTEM FOR ATHLETICS AND PHYSICAL REHABILITATION INCLUDING STUDENT UNIT AND REMOTE UNIT COMMUNICABLE THEREWITH, and U.S. Provisional Patent Application No. 60/719,161 filed Sep. 21, 2005 entitled MONITORING, EVALUATION AND TRAINING SYSTEM FOR ATHLETICS AND PHYSICAL REHABILITATION INCLUDING STUDENT UNIT AND REMOTE UNIT COMMUNICABLE THEREWITH, are incorporated herein by reference in their entirety.

FIG. 1 depicts a conventional orientation and motion-sensing device 110 attached to the head of a user. For example, the conventional device 110 may be attached to a headband 120 using one or more Velcro™ fasteners. As shown in FIG. 1, the device 110 may be attached to the user's headband to position the device over his or her right ear. The device 110 includes a number of tilt indicators (not shown) operative to detect and monitor the orientation of the user's head, i.e., the direction and magnitude of tilt, relative to a reference orientation and/or to an adjustable tilt magnitude threshold. For example, the device 110 may be employed to monitor the direction and magnitude of tilt of the user's head while the user plays tennis. To establish the reference orientation, the user mounts the device 110 over his or her right ear, and assumes a suitable tennis posture such as a vertical stance. The device 110 then measures the tilt of the device relative to X and Y-axes 130 and 140 of the user's head to establish the reference orientation. After the reference orientation has been established, the device 110 monitors the tilt of the user's head, e.g., from left to right, from right to left, from front to back, and/or from back to front, while the user plays tennis. If the magnitude of tilt in any direction exceeds the adjustable magnitude threshold, then a visible and/or audible alarm is generated to indicate the dominant direction of tilt.

Proper operation of the conventional orientation and motion-sensing device 110 of FIG. 1 depends highly upon the positioning and orientation of the device 110 relative to the user's head. For example, if the user were to position the device 110 over the left ear instead of the right ear, as depicted in FIG. 1, then the device 110 would incorrectly interpret head tilting from front to back as tilting from back to front, and head tilting from left to right as tilting from right to left. In addition, as shown in FIG. 1, the X-axis 150 of the device 110 is not precisely aligned with the X-axis 130 of the user's head, i.e., the X-axis 130 of the user's head points slightly to the right of the X-axis 150 of the device 110. As a result, the device 110 may provide inaccurate directional feedback to the user, especially when the user tilts his or her head in the front-left, front-right, back-left, or back-right directions.

FIGS. 2a-2e depict an illustrative embodiment of an orientation and motion-sensing device 210, in accordance with the present invention. The orientation and motion-sensing device 210 provides proper operation and increased accuracy when attached in substantially any orientation relative to the user, and accurately measures changes in body-part orientation whether or not these changes are in directions aligned with the device's sensitive axes. In addition, the device 210 provides a technique for calibrating a reference orientation of the user so that the device correctly tracks changes in the user's posture or body orientation. The device 210 also maintains high sensitivity and accuracy as a sensitive axis of the device becomes vertical, reduces the generation of erroneous or misleading signals in the presence of acceleration, and estimates the magnitude and direction of the acceleration. In addition, the device 210 provides visible, audible (e.g., human speech), and/or tactile feedback to the user.

FIG. 2a depicts the orientation and motion-sensing device 210 attached to the head of a user. As shown in FIG. 2a, the device 210 may be attached to a golf cap 220 using one or more Velcro™ fasteners. It should be understood, however, that the device 210 may alternatively be attached directly or indirectly to any other suitable body part of the user, or any suitable article of clothing or accessory of the user, using any other suitable type of fastener. Further, the device 210 may be incorporated into an article of clothing or accessory, may be held by the user, may be held against the user by an attendant, or may be incorporated into a hand-held device such as a cell phone, a computer game control, or any other suitable hand-held device. In the presently disclosed embodiment, the device 210 is configured to provide one or more visible and/or audible indications of the orientation or movement of the user's body in real time. For example, the device 210 may be employed to monitor the orientation or movement of the user as he or she engages in a sporting or leisure activity such as golf, tennis, fencing, sculling, running, walking, bicycling, dancing, or any other suitable activity. The device 210 may also be employed by physical therapy patients as an aid in performing rehabilitation exercises or to palliate the effects of a loss of balance ability, which may have resulted from an accident, physical and/or mental degradation, or illness.

For example, if the device 210 is attached to the user's head, as depicted in FIG. 2a, then the device 210 may be used to monitor the tilt of the user's head while he or she plays golf. Specifically, the device 210 is operative to monitor the tilt of the user's head relative to an X-axis 230 (see FIG. 2e) and a Y-axis 235 (see FIG. 2b) of the device 210. In the illustrated embodiment, the X-axis 230 points approximately straight ahead of the user and the Y-axis 235 points approximately toward the right side of the user when the device 210 is attached to the user's cap, as depicted in FIG. 2a. In this exemplary embodiment, the device 210 monitors the tilt of the user's head, e.g., from left to right, from right to left, from front to back, and from back to front, while the user plays golf. FIG. 3 is a diagram illustrating the various approximate head tilts (i.e., front, back, left, right) of the user relative to the X and Y-axes 310 and 320.

Figure 2B:
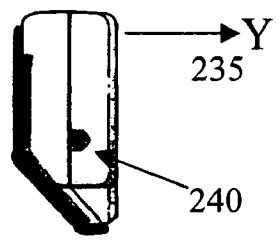
Figure 2C:
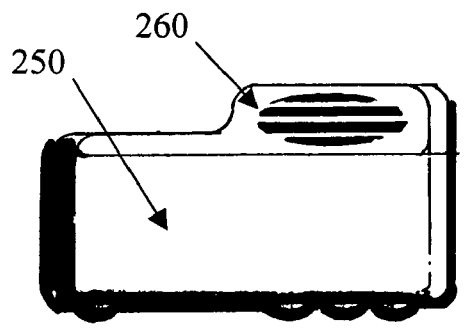
Figure 2D:
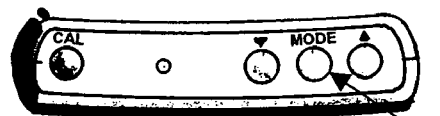
Figure 2E:
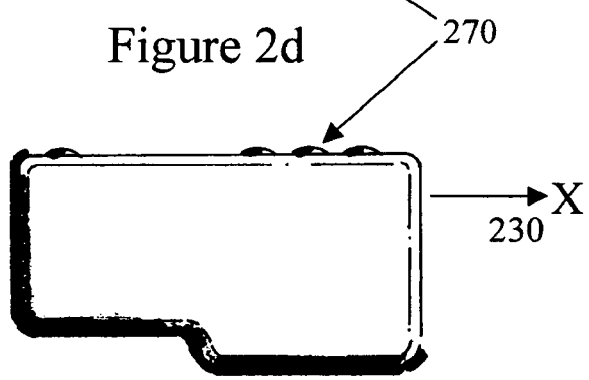
Figure 3:
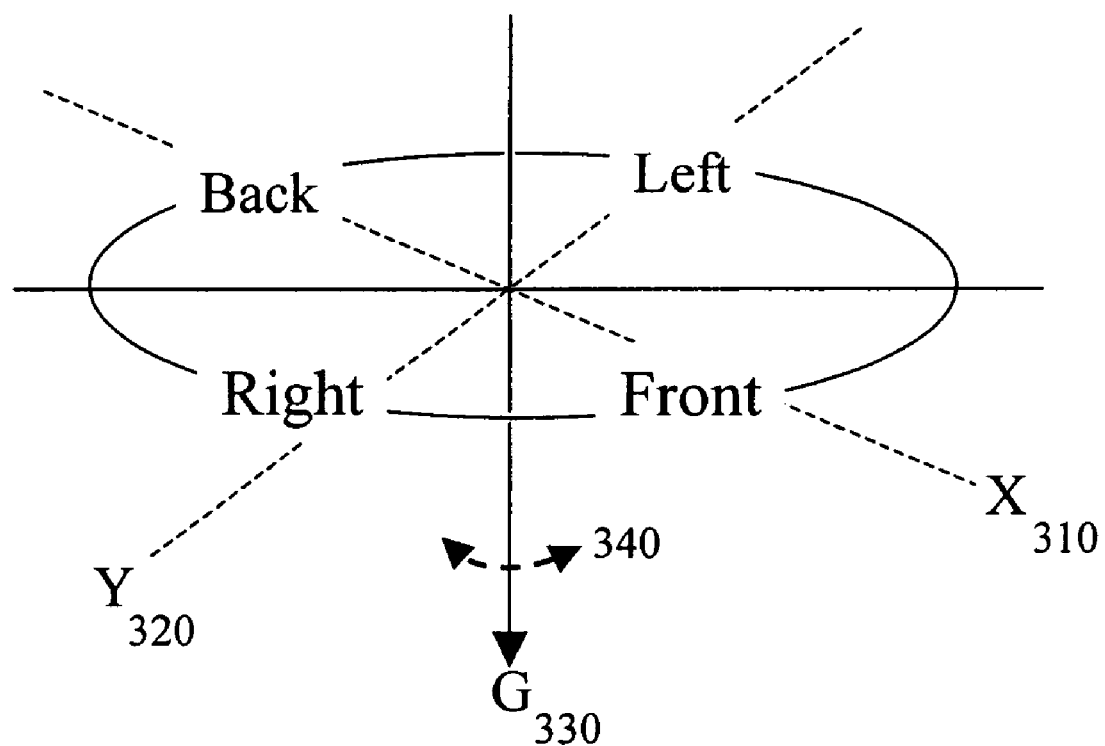
FIG. 3 illustrates a feedback pattern of the device of FIG. 2a with reference to various head orientations of a user.

FIG. 2b depicts a back-end view of the orientation and motion-sensing device 210, illustrating a connector 240 for receiving a headphone or earphone jack (not shown). In other embodiments, connector 240 may be designed to accommodate a battery-charger connector or a network connector, or may be excluded from the system. FIG. 2c depicts a backside view of the device 210 including an inner surface 250 that would normally be disposed against the user, and a speaker 260. In alternative embodiments, one or more visible, alphanumerical, tactile, and/or graphical outputs may be provided instead of, or in addition to, the audible output provided by the headphone/earphone 240 (not shown) or the speaker 260. FIG. 2d depicts a top view of the device 210 including four user controls 270 (e.g., cal, ∇, mode, Δ) implemented as pushbuttons, and a light emitting diode (LED; not numbered). FIG. 2e depicts an exemplary front side view of the device 210.

Figure 4:
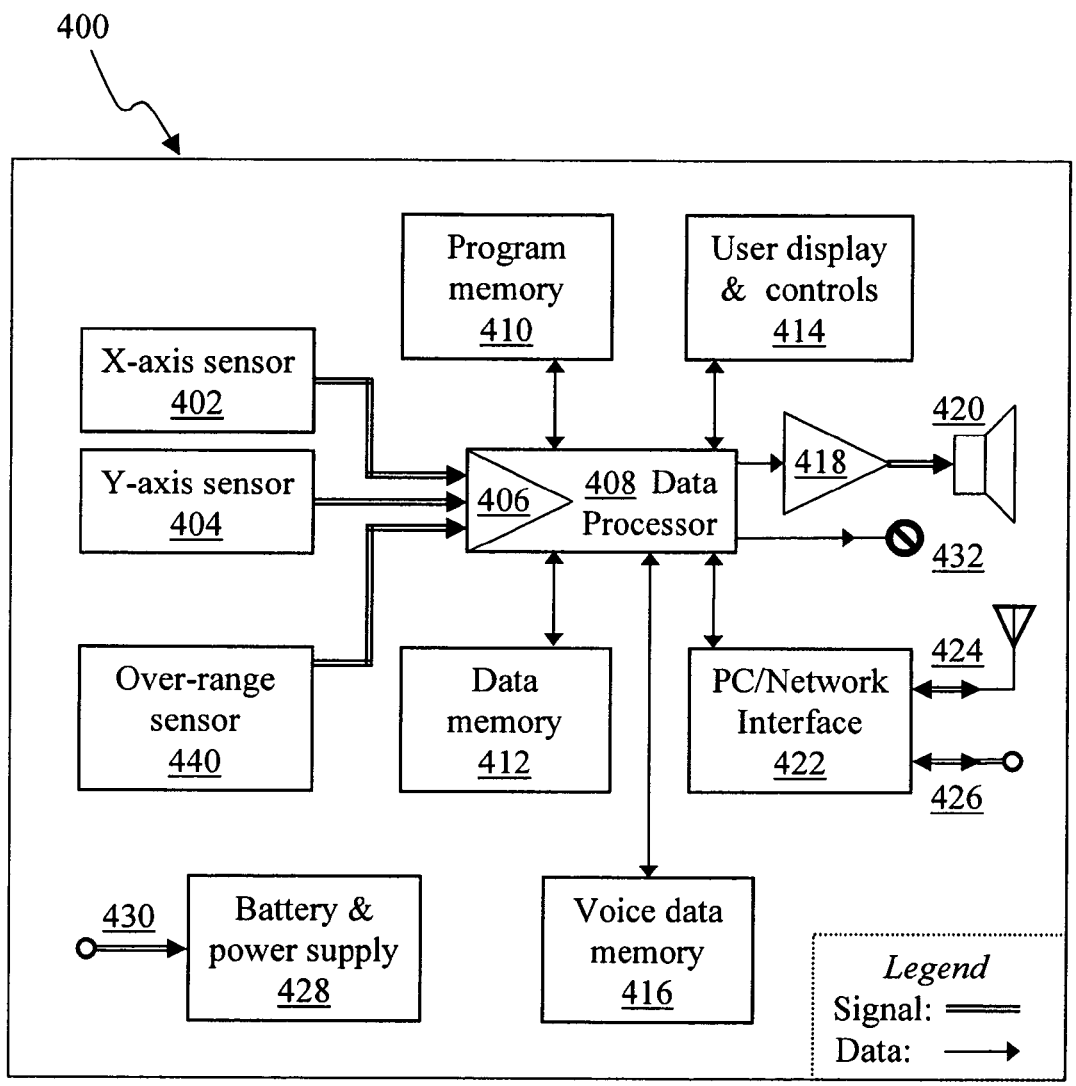

FIG. 4 depicts exemplary functional components 400 included in the orientation and motion-sensing device 210 (see FIGS. 2a-2e). As shown in FIG. 4, the functional components 400 include an X-axis sensor 402, a Y-axis sensor 404, a signal multiplexer and analog-to-digital converter (A/D) 406, a data processor 408, a program memory 410, a data memory 412, a user display and controls section 414, a voice data memory 416, an audio output converter 418, a speaker 420, a PC/network interface 422, a wireless networking antenna 424, a wired networking connector 426, a battery and power supply 428, a battery charger connector 430, one or more tactile vibration outputs 432, and an over-range sensor 440. In embodiments that include more than one tactile sensor, Front/Back/Left/Right tilt indications can be signaled respectively by, for example, the activation of a tactile vibration sensor attached to the inside of a headband at the forehead, the back of the skull, the left temple, and the right temple. When charging, the battery charger connector 430 is connected to a battery charger (not shown). When in a network configuration, the PC/network interface 422 is connected to a personal computer (PC; not shown), and/or to a point-to-point network/remote-control unit, a local area network (LAN), or a wide area network (WAN) through either the wireless networking antenna 424 or the wired networking connector 426. It is noted that alternative embodiments of the orientation and motion-sensing device 210 may include all or a subset of the functional components illustrated in FIG. 4. For example, in some embodiments, the components 416, 418, 420, 422, 424, 426, 430, 432, and/or 440 may be omitted. In the presently disclosed embodiment, the X-axis sensor 402 and the Y-axis sensor 404 are accelerometers oriented within the device 210 so that their respective sensitive axes, namely, the X-axis 230 and the Y-axis 235, are positioned 90° to one another. It is noted, however, that the X and Y-axis sensors 402 and 404 may employ any other suitable technique for sensing tilt, and may be oriented at any other suitable angle relative to one another.

The X-axis sensor 402 is operative to sense tilt along the X-axis 230 (see FIG. 2e) of the device 210, and the Y-axis sensor 404 is operative to sense tilt along the Y-axis 235 (see FIG. 2b) of the device 210. The X and Y-axis sensors 402 and 404 sense tilt and acceleration along the X and Y axes 230 and 235, respectively, by measuring the projection of a force vector on their respective axes that is the sum of the force of gravity at the location of the device 210 and a force of acceleration applied to the device 210 during use. This force vector is known interchangeably as an apparent acceleration vector or an apparatus gravity vector. FIG. 3 depicts the relationship between the X and Y axes 310 and 320 and an exemplary apparent gravity vector G 330. In the description of the operation of the device 210 provided below, the frame of reference is the X and Y axes 310 and 320 of the device 210, while the direction of the apparent gravity vector G 330 relative to the X and Y axes 310 and 320 can change over time, as indicated by a directional arrow 340.

For example, each of the X and Y-axis sensors 402, 404 may be a micro-machined accelerometer such as the ADXL103 accelerometer sold by Analog Devices Inc., Norwood, Mass., U.S.A. Alternatively, the X and Y-axis sensors 402, 404 may be implemented using a single dual-axis accelerometer such the ADXL322 dual-axis accelerometer sold by Analog Devices Inc. In addition, the signal multiplexer and analog-to-digital converter (A/D) 406 and the data processor 408 may be implemented using the PIC16F777 microcontroller sold by Microchip Technology Inc., Chandler, Ariz., U.S.A., or any other suitable microcontroller or microprocessor. In addition, the audio converter 418 and the voice data memory 416 may be implemented using the ML22Q54 signal processor sold by OKI Semiconductor, Sunnyvale, Calif., U.S.A., or any other suitable device for storing and processing audio files. In one embodiment, conversion of the voice files is performed using software executing on the data processor 408 instead of being implemented as the separate functional block 418. In addition, the PC/network interface 422 may be a wired or wireless (e.g., infrared or RF) interface for downloading or uploading content to or from the program memory 410, the data memory 412, and/or the voice data memory 416. The PC/network interface 422 may also be configured for controlling the device 210 remotely. Time-stamps and/or sequences of measurements performed by the orientation and motion-sensing device 210 may be stored within the data memory 412 for subsequent local processing, for subsequent feedback to the user, and/or for subsequent uploading to a computer via the PC/network interface 422. In addition, application-specific user feedback phrases, measurement algorithms, and/or cuing sequences may be downloaded to the device 210 from a computer or over a communications network such as the Internet.

The over-range sensor 440 operates as a third tilt sensor, which is oriented at a specified angle to the X-Y plane defined by the sensitive X and Y-axes 310, 320. In one embodiment, the sensitive axis of the over-range sensor 440 is oriented at 90° to the X-Y plane. Like the X and Y-axis sensors 402 and 404, the over-range sensor 440 may be a micro-machined accelerometer such as the ADXL103 accelerometer sold by Analog Devices Inc. Alternatively, the X-axis sensor 402, the Y-axis sensor 404, and the over-range sensor 440 may be implemented using a single micro-machined 3-axis accelerometer such as the ADXL330 accelerometer sold by Analog Devices Inc.

Figure 5:
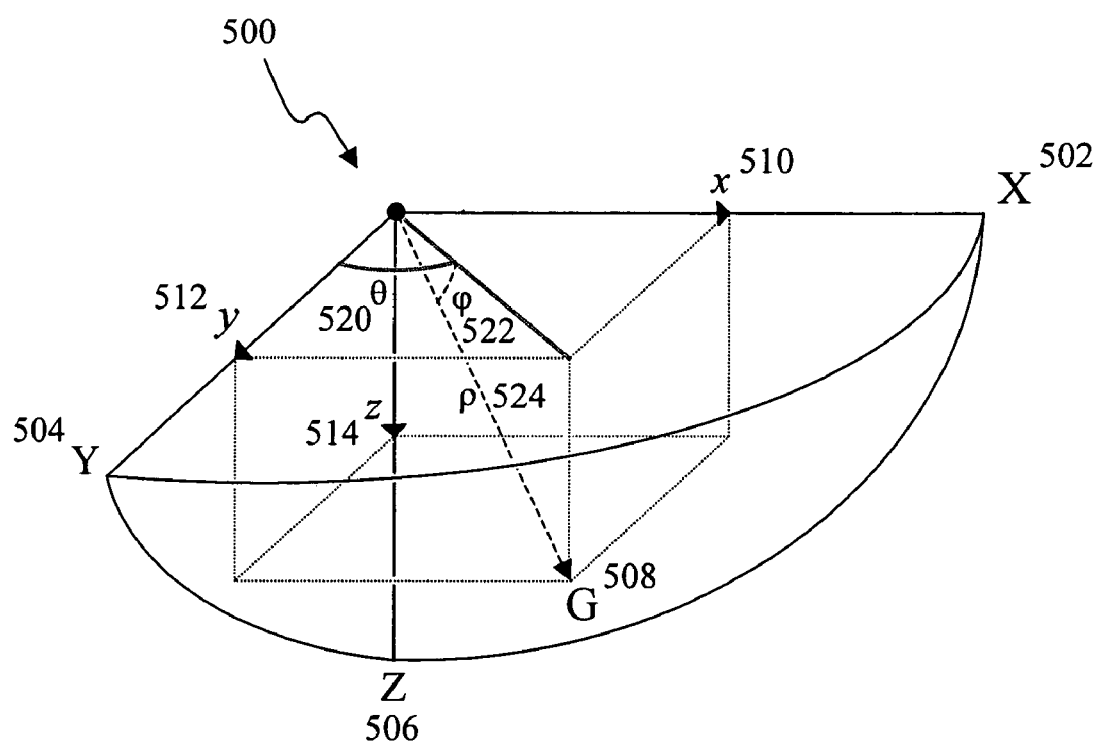

FIG. 5 is a diagram of a geometric model 500 that may be employed to illustrate the operation of the orientation and motion-sensing device 210 (see FIGS. 2a-2e). Specifically, the geometric model 500, which is constructed with reference to both the spherical and Cartesian coordinate systems, may be used to quantify the device's orientation and acceleration, and to quantify the alignment of the device 210 with the body part to which it is attached. The geometric model 500 includes the entire unit sphere, of which one octal portion is shown. Further, an X-axis 502 represents the sensitive axis of the X-axis sensor 402 (see FIG. 4), a Y-axis 504 represents the sensitive axis of the Y-axis sensor 404 (see FIG. 4), and a Z-axis 506 represents the sensitive axis of the over-range sensor 440 (see FIG. 4). The X and Y-axes 502 and 504 define an X-Y plane, and the Z-axis 506 is oriented 90° to the X-Y plane. In addition, FIG. 5 depicts one possible direction of an exemplary apparent gravity vector G 508. The origin of the vector G corresponds to the origin of the unit sphere. Because the actual gravity vector always points in the same direction, i.e., toward the center of the earth, the device 210 can determine changes in the orientation and acceleration of the body part to which it is attached by monitoring and analyzing changes in the magnitude and direction of the apparent gravity vector G 508 relative to axes X 502, Y 504 and Z 506.

Within the geometric model 500, the length x of an X-vector 510 represents the magnitude of the apparent gravity vector G 508 as measured by the X-axis sensor 402 along the X-axis 502, and the length y of a Y-vector 512 represents the magnitude of the apparent gravity vector G 508 measured by the Y-axis sensor 404 along the Y-axis 504. Similarly, the length z of a Z-vector 514 represents the magnitude of the apparent gravity vector G 508 measured by the over-range sensor 440 along the Z-axis 506. It is noted that the direction of the apparent gravity vector G 508 can be defined by angles $\theta$ 530 and $\phi$ 522. Accordingly, the direction of the apparent gravity vector G 508 can be determined using the measurements provided by the X and Y-axis sensors 402 and 404 (see FIG. 4). It is noted that, in an alternative embodiment, the X-axis 502 and the Y-axis 504 may be oriented at an angle different from 90° to one another, in which case the formulas below may be modified as appropriate using known trigonometric identities.

Those of ordinary skill in this art will appreciate that an accelerometer's sensitivity to changes in tilt is at a maximum when the sensitive axis of the accelerometer is close to horizontal, and is at a minimum when the sensitive axis of the accelerometer becomes vertical. In the presently disclosed embodiment, the orientation and motion-sensing device 210 (see FIGS. 2a-2e) employs the over-range sensor 440 (see FIG. 4) in conjunction with the X and Y-axis sensors 402 and 404 (see FIG. 4) to determine the direction of the apparent gravity vector G 508 over the entire unit sphere, thereby allowing the device 210 to provide an accurate measurement of tilt in any orientation of the device.

Specifically, as discussed above, the length of the X-vector 510, the length of the Y-vector 512, and the length of the Z-vector 514 represent the magnitudes of acceleration measured by the X-axis sensor 402, the Y-axis sensor 404, and the over-range sensor 440, respectively, when the device 210 is acted upon by the apparent gravity vector G 508. In the absence of acceleration, the length $\rho$ 524 (see FIG. 5) of the apparent gravity vector G 508, normalized to the gravitational field at the earth's surface, may be expressed as $$\rho^2 = x^2 + y^2 + z^2 = 1. \tag{1}$$

It is noted that representation of the direction $\theta$ 520 and $\phi$ 522, and the length of $\rho$ 524, of G 508 is in the spherical coordinate system for illustrative purposes only, and that all of the angles and formulas expressed in this application can be represented and expressed equivalently in other 3-dimensional coordinate systems by those of ordinary skill in this art.

To extend the calculation of the angles θ 520 and φ 522 of the vector G 508 to orientations of device 210 (see FIGS. 2*a*-2*e*) where the sensitive axis of either the X-axis sensor 402 or the Y-axis sensors 404 is more vertical than the sensitive axis of the over-range sensor 440, an appropriate substitution between variables x, y and z is performed using formula (1) so that the two most-horizontal sensors are used for each calculation. The angles θ 520 and φ 522 of the vector G 508 may then be determined. In this way, the measurement provided by the single over-range sensor 440 can be used to extend the calculation of the angles θ 520 and φ 522 of the vector G 508 over the entire unit sphere without loss of precision.

It is noted that the accuracy of the measurement of the direction of the apparent gravity vector G by the orientation and motion-sensing device 210 (see FIGS. 2*a*-2*e*) can decrease when the device undergoes acceleration. Whether or not the device 210 is undergoing acceleration, and how much the acceleration is affecting the accuracy of the measurement of the apparent gravity vector G by the device, can be determined based upon the calculated length ρ 524 of the apparent gravity vector G, using formula (1) without substitution between the three variables x, y and z. For example, if the length ρ 524 is greater than or less than 1 (ρ>1, ρ<1), then it may be concluded that the device 210 is being subjected to acceleration in addition to the force of gravity. It is noted that for small changes in the value of ρ, the worst-case error in the calculation of the direction of the apparent gravity vector G is about 1° for a 1.75% change in ρ. In one embodiment, if the error in the calculation of the apparent gravity vector G is significant for a given application, then the device 210 provides a suitable visible, tactile and/or audible warning to the user.

Figure 6:
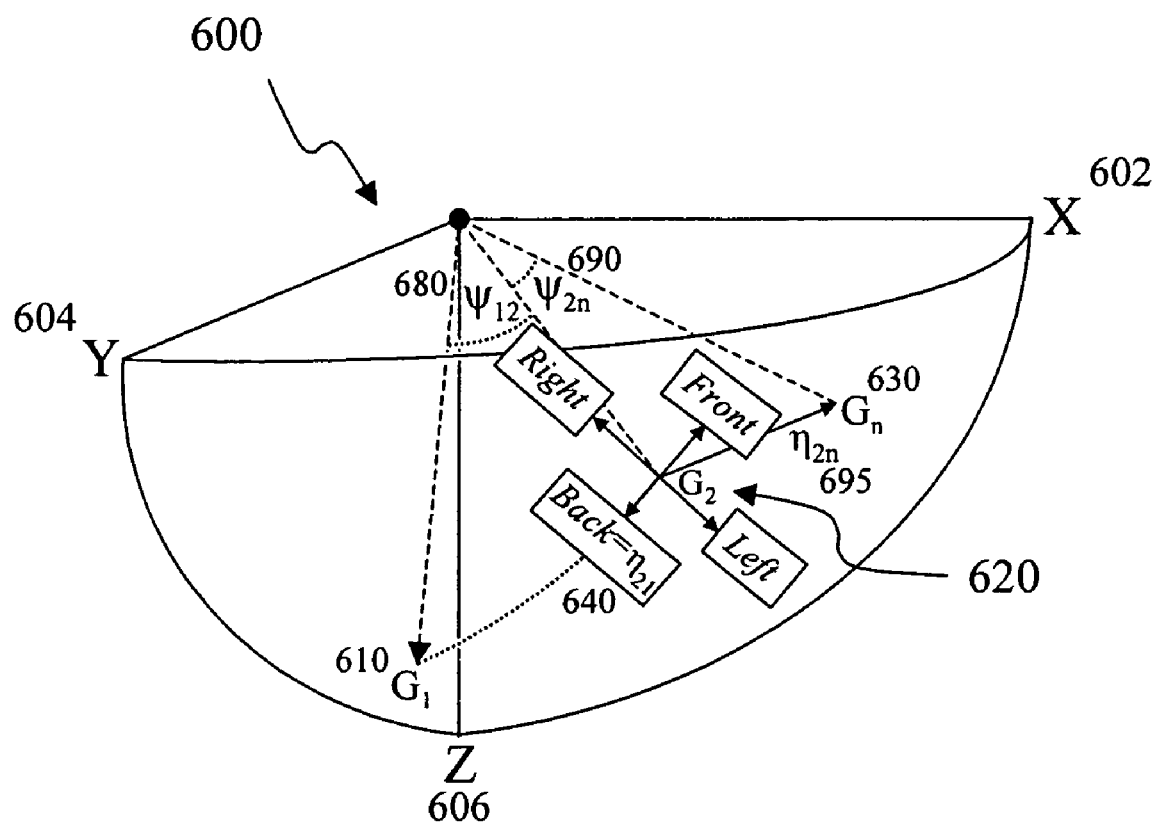
FIG. 6 is a diagram of a geometric model illustrating a sequence of user movements that may be performed to calibrate the alignment between the device of FIG. 2a and a reference orientation of the user, and how to determine the direction and magnitude of subsequent user deviation from the reference orientation.

FIG. 6 is a diagram of a geometric model 600 that may be employed to illustrate a technique of determining the orientation of the device 210 (see FIGS. 2*a*-2*e*) relative to a body part of a user to which it is attached. Like the geometric model 500 of FIG. 5, the geometric model 600 of FIG. 6 is constructed with reference to both the spherical and Cartesian coordinate systems and displays one octal portion of a unit sphere. Further, an X-axis 602 represents the sensitive axis of the X-axis sensor 402 (see FIG. 4), a Y-axis 604 represents the sensitive axis of the Y-axis sensor 404 (see FIG. 4), and a Z-axis 606 represents the sensitive axis of the over-range sensor 440.

Figure 7:
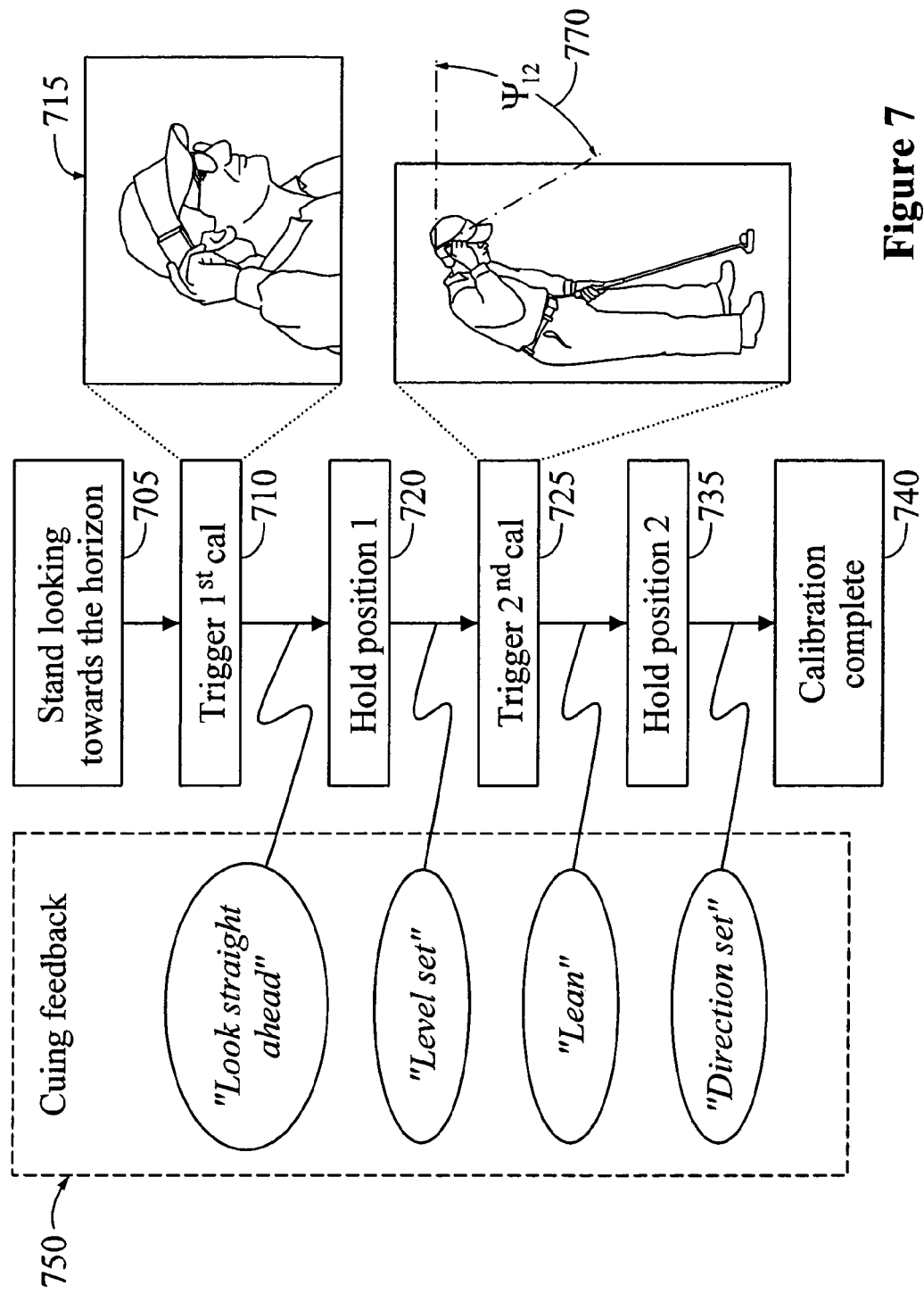
FIG. 7 is a flow diagram of a method of calibrating the device of FIG. 2a, corresponding to the sequence of user movements of FIG. 6.

An illustrative method of calibrating the alignment of the device 210 with the body part to which it is attached is described below with reference to FIGS. 6 and 7. The method of FIG. 7 provides a sequence of steps for quantifying the orientation of the device 210 relative to the body part to which it is attached, and allows the determination of a reference orientation of the user. In this illustrative method, the device is attached to the user's golf cap above his or her right ear (see, e.g., illustration 715 of FIG. 7). It is understood, however, that the device 210 may alternatively be attached to any other suitable body part (e.g., the user's chest, back, elbow, etc.), and in any other suitable orientation relative to the user. This is because the X and Y-axes of the device 210 are not required to be aligned with the corresponding axes of the body part to which it is attached, nor does the degree of misalignment need to be known.

According to the calibration method of FIG. 7, the user first stands vertically, looking towards the horizon, as depicted in step 705. It is noted that the user may alternatively look in any other suitable direction. Next, the user triggers a first calibration of the device 210 at time 1 by depressing one or more suitable user controls (see, e.g., the cal pushbutton 270 of FIG. 2), as depicted in step 710. The user then holds his or her vertical standing orientation, as depicted in step 720, while the device 210 captures the first calibration direction of the apparent gravity vector G, as indicated by the vector $G_1$ 610 (see FIG. 6). As shown in FIG. 6, the vector $G_1$ 610 does not necessarily coincide with the Z-axis 606 of the device 210. In other words, the X and/or Y axes 602, 604 of the device 210 are not required to be horizontal. Next, the user tilts his or her head a number of degrees toward the front or forward direction, and triggers a second calibration of the device 210 at time 2 by depressing the cal pushbutton 270, as depicted in step 725. It is noted that the user may alternatively tilt his or her head in any other suitable direction. It is further noted that, in an alternative embodiment, the device 210 may be configured to execute the triggering steps 710 and 725 under program control, allowing the calibration procedure to be performed without requiring the user to manipulate the device. The user then holds the tilted orientation of his or her head, as depicted in step 735, while the device 210 captures the second calibration direction of the apparent gravity vector G, as indicated by the apparent gravity vector $G_2$ 620 (see FIG. 6). The data-capture phase of the calibration is then complete as indicated in step 740.

The device 210 employs the first and second calibration directions of the apparent gravity vector G to determine the orientation of the device relative to the body part to which it is attached, and the reference orientation of the user. As illustrated in FIG. 6, an arc $G_1 \rightarrow G_2$ extending from the end of the apparent gravity vector $G_1$ 610 to the end of the apparent gravity vector $G_2$ 620 is a great circle segment on the unit sphere whose direction at each point is the direction of forward angular tilt of the user at that point. It is noted that subsequent tilting of the user's head exactly in the forward direction will cause the end of the apparent gravity vector G to extend the path defined by the great circle arc $G_1 \rightarrow G_2$. FIG. 6 illustrates an example of a continued tilt beyond the vector $G_2$ 620, slightly to the left of straight ahead at time n, resulting in the apparent movement of the end of the vector G to a point corresponding to the end of the vector $G_n$ 630 at time n. Left and Right directions are inverted because the perspective of FIG. 6 is from outside the sphere looking in, whereas the user's perspective is from the center of the sphere looking out.

This method is valid for end-points of the vectors $G_1$ 610, $G_2$ 620, and $G_n$ 630 located anywhere on the unit sphere, so the device can be mounted in any orientation relative to the user, while allowing accurate determination of the orientation of the device relative to the body part to which it is attached, and of the reference orientation of the user.

In the illustrated embodiment, the magnitude of forward tilt of the user's head below the horizontal plane 770 (see FIG. 7) at time 2 corresponds to an angle $\psi_{12}$ 680 representing the change in direction from $G_1$ 610 to $G_2$ 620. The angle $\psi_{12}$ is equivalent to the length of the great circle segment $G_1 \rightarrow G_2$ and, applying known rules of trigonometry, may be determined from the expression $$\cos \psi_{12} = (\sin \phi_1 * \sin \phi_2) + (\cos (\theta_2 - \theta_1) * \cos \phi_1 * \cos \phi_2). \quad (2)$$

With respect to the user's orientation, a back tilt 640 is in the direction $\eta_{21}$, which is the direction of the great circle arc $G_2 \rightarrow G_1$ at the point located at the end of the apparent gravity vector $G_2$. Applying known rules of trigonometry, the direction $\eta_{21}$ in the spherical coordinate system may be determined from the expression $$\cos \eta_{21} = (\sin \phi_1 - (\sin \phi_2 * \cos \psi_{12}))/(\cos \phi_2 * \sin \psi_{12}) \quad (3)$$

and, similarly, the direction of the user's subsequent tilt $\eta_{2n}$ 695 at time n can be determined by:

$$\cos \eta_{2n} = (\sin \phi_n - (\sin \phi_2 * \cos \psi_{n2}))/(\cos \phi_2 * \sin \psi_{n2}) \quad (4)$$

In the illustrated embodiment of the method, the device 210 generates an audible message "Front" if tilts subsequent to the calibration are ±45° from the user's Front direction, an audible message "Left" if tilts are ±45° from the Left direction, an audible message "Back" if tilts are ±45° from the Back direction, and an audible message "Right" if tilts are ±45° from the Right direction. The correct feedback from the device 210 can thus be expressed mathematically as "Back" if $\eta_{21} - 45° < \eta_{2n} < \eta_{21} + 45°$ \quad (5)

"Right" if $\eta_{21} + 45° < \eta_{2n} < \eta_{21} + 135°$ \quad (6)

"Forward" if $\eta_{21} + 135° < \eta_{2n} < \eta_{21} + 225°$ \quad (7)

"Left" if $\eta_{21} + 225° < \eta_{2n} < \eta_{21} + 315°$, \quad (8)

and the magnitude of tilt $\psi_{2n}$ 690 (see FIG. 6) at time n relative to the second calibration orientation may be determined from the expression $$\cos \psi_{2n} = (\sin \phi_2 * \sin \phi_n) + (\cos (\theta_n - \theta_2) * \cos \phi_2 * \cos \phi_n), \quad (9)$$

where angle $\psi_{2n}$ is the length of the great circle segment $G_2 \rightarrow G_n$.

Figure 8:
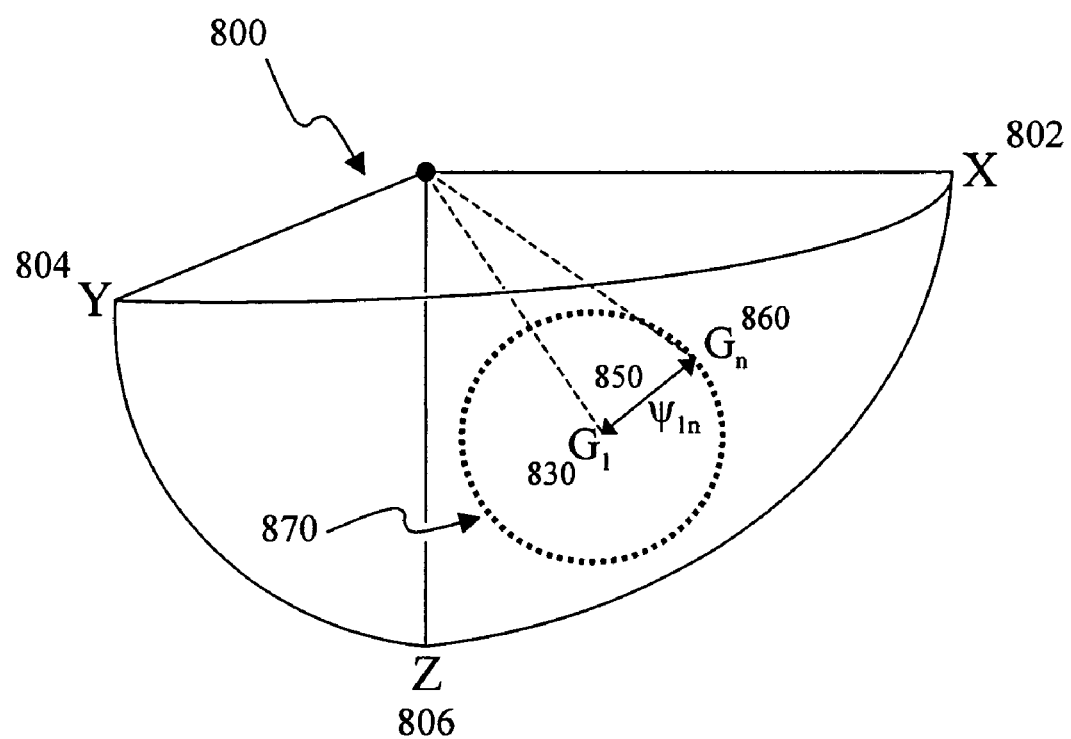
FIG. 8 is a diagram of a geometric model illustrating an alternate sequence of user movements that may be performed when calibrating the device of FIG. 2a, and how to determine the magnitude of subsequent deviation from the calibrated orientation.

FIG. 8 is a diagram of a geometric model 800 that may be employed to illustrate the operation of the orientation and motion-sensing device 210 (see FIGS. 2a-2e) in applications including a physical rehabilitation and evaluation application involving the determination of a patient's range of motion (ROM). In this illustrative mode of operation, the orientation of the device 210 relative to the body part is fixed but indeterminate, and the direction of the body part motion to be measured is in a vertical plane, but in an unknown direction. This method is thus useful when range of motion in several different directions is to be measured without having to reposition the device between measurements. The geometric model 800 of FIG. 8 is constructed with reference to both the spherical and Cartesian coordinate systems. Only one octal portion of the unit sphere is shown. An X-axis 802 represents the sensitive axis of the X-axis sensor 402 (see FIG. 4), a Y-axis 804 represents the sensitive axis of the Y-axis sensor 404 (see FIG. 4), and a Z-axis 806 represents the sensitive axis of the over-range sensor 440. In this application, the device 210 employs a single orientation calibration at time 1, as indicated by the apparent gravity vector $G_1$ 830 (see FIG. 8). For example, the vector $G_1$ 830 may correspond to the resting or starting orientation of a limb extension. As the patient extends his or her limb, the end of the apparent gravity vector G moves away from the end of the vector $G_1$ 830. Because the orientation of the device relative to the body part is fixed but indeterminate, the end of apparent gravity vector $G_n$ 860, corresponding to an intermediary or maximum extension, may be located anywhere on a circle 870. The magnitude of extension, which is represented by the magnitude of tilt $\psi_{1n}$ 850 (see FIG. 8) is the length of the great circle segment $G_1 \rightarrow G_n$ where $\psi_{1n}$ can be calculated using the expression $$\cos \psi_{1n} = (\sin \phi_1 * \sin \phi_n) + (\cos (\theta_n - \theta_1) * \cos \phi_1 * \cos \phi_n). \quad (10)$$

It is noted that the device 210 may be configured to monitor, capture and store the maximum value of the magnitude of tilt $\psi_{1n}$ for subsequent feedback, thereby allowing the patient to reduce the amount of time needed to hold a limb extension, potentially to a fraction of a second.

As described above, the presently disclosed orientation and motion-sensing device 210 (see FIGS. 2a-2e) includes the voice data memory 416, the data processor 408, the audio processor 418, and the speaker 420 (see FIG. 4), which may be configured to provide a sequence of distinguishable audible cues and action confirmations to the user while he or she performs the calibration method of FIG. 7 or any other suitable function of the device 210. FIG. 7 depicts exemplary audible cues and action confirmations 750 in the English language that may be provided by the device 210 after the user performs the acts depicted in steps 710, 720, 725, and 735. The audible cues and action confirmations 750 are designed to facilitate and confirm proper execution of the various steps in the calibration procedure. For example, the device 210 may be configured to provide the audible cue "Look straight ahead" after step 710. Further, the device 210 may provide the audible confirmation "Level set" after step 720, the audible cue "Lean" after step 725, and the audible confirmation "Direction set" after step 735. It is understood that in alternative embodiments, the device 210 may be configured to provide any other suitable audible, visible, and/or tactile cues and action confirmations to the user, using any other suitable language, in order to facilitate device operation. For example, the device 210 may include one or more vibrating transducers (not shown) to provide one or more tactile cues and/or action confirmations against the user's skin.

The orientation and motion-sensing device 210 may also be configured to provide user feedback in the form of audible phrases stored in the voice data memory 416 or synthesized by the device. The audible user feedback phrases may be constructed and selected by the device 210 under control of the data processor 408, which may sequence the phrases in response to user motions monitored by the device. The calibration method of FIG. 7 includes an exemplary use of such phrases as cues to guide the user in executing specific and desired motions (e.g., "Look straight ahead"), and to confirm to the user the proper or improper execution of a step or sequence of steps (e.g., "Level set", "Direction set"). Such audible user feedback phrases may also be employed in physical rehabilitation and evaluation applications to cue the user while performing physical therapy exercises, e.g., "Raise your arm slowly as far as it can go", "Stand on your right foot until you are told to stop", "The left elbow flexion will now be measured", or "Attach the device to the left wrist and stabilize the humerus". Suitable sequences of user guidance and feedback phrases can be programmed into the device 210, for example through the PC/Network Interface 422 (see FIG. 4) according to a specific plan of desired user motions, in response to an analysis of user motions, or a combination thereof.

In addition, the orientation and motion-sensing device 210 may be configured to provide audible performance feedback to the user that is contextual to a specific application. For example, in a sports training application, the desired performance feedback in response to a tilt in the forward direction may be "You are leaning forward", while in a balance training exercise, the desired performance feedback in response to the same forward tilt may be "Go Back", "Keep your head up", or "You are about to fall over". In a physical therapy application, the desired performance feedback in response to a maximum limb extension that is below a specified lower limit may be "Stretch a little farther", while the desired performance feedback in response to exceeding a specified upper limit may be "You've gone too far". In an application for determining a patient's range of motion (ROM), the desired performance feedback may be "Your extension is 85°", "Your maximum extension was 135°" or, in the case of blind measurements, the desired performance feedback may be "Measurement number 4 has been recorded". The device 210 may also provide feedback that tracks user progress, using phrases such as "Repetition three completed, seven more to go", or "Your average head tilt over the past five minutes was 5° and your average direction was 45° to the right of straight ahead". In addition, the device 210 may provide user feedback corresponding to the number of times a local minimum or maximum point satisfying certain specified conditions has been reached.

As described above, the orientation and motion-sensing device 210 may be incorporated into a hand-held device such as a cell-phone or a computer game control. For example, in a cell-phone application, the device 210 may be configured to announce the phrase "Call sent to voice-mail" in response to an outward flick of the user's wrist, e.g., when there is a call waiting. In a computer game application, the device 210 may be configured to announce the phrase "Your opponent is defeated" after the user has moved the device through a correct sequence of target orientations. In addition, the device 210 may be configured to allow selection and/or programming, via the PC/Network Interface 422, of a particular individual's voice, e.g., a teacher, a sports celebrity, etc., or a particular language, e.g., English, French, German, Italian, Chinese, Japanese, Korean, etc., to provide the user feedback.

In addition, the orientation and motion-sensing device 210 (see FIGS. 2a-2e) may be configured to initiate a particular operational mode in response to a specified sequence of user movements. For example, the device 210 may be configured to initiate a posture-monitoring operational mode in response to a specified sequence of movements while the user is practicing or participating in a round of golf. In this way, the user can initiate the posture-monitoring mode of the device 210 without having to release his or her golf club. In one embodiment, the sequence of user movements includes at least two steps performed in a specified order, in which each step requires the user to look in a specified direction. The device 210 may provide audible, visible, and/or tactile confirmation of the proper execution of the ordered steps. The sequence of user movements is designed to assure that the user is unlikely to perform the movements unintentionally.

For example, after performing the calibration method of FIG. 7, a user engaged in a round of golf may initiate the posture monitoring mode of the device 210 by performing a specified sequence of movements, which, based on the resulting orientations of the device 210 relative to the user, effectively causes the apparent gravity vector G to retrace the path from a direction corresponding to the vector $G_2$ 620 (see FIG. 6) to a direction corresponding to the vector $G_1$ 610 (see FIG. 6), and back to the direction corresponding to the vector $G_2$ 620. In a golfing application, the specified and corresponding sequence of user movements may include addressing the golf ball, looking at the horizon, and addressing the golf ball again. Further, the device 210 may provide audible, visible, and/or tactile confirmations of the proper execution of each user movement in the specified sequence. Moreover, a tolerance circle may be provided around the locations of the vectors $G_2$ and/or $G_1$ so that the user is not required to look exactly at a particular point on the horizon or to address the golf ball in a precise manner in order for the device 210 to recognize the user's intent to initiate a particular operational mode. For example, a tolerance circle of 10° or any other suitable size may be provided. In an alternative embodiment, the directions of the vectors $G_1$ and $G_2$ corresponding to the first and second target orientations of the device 210 may be replaced by two other orientations that are related geometrically to the directions of the vectors $G_1$ and $G_2$, so long as these orientations correspond to convenient visual targets for the user.

Figure 9A:
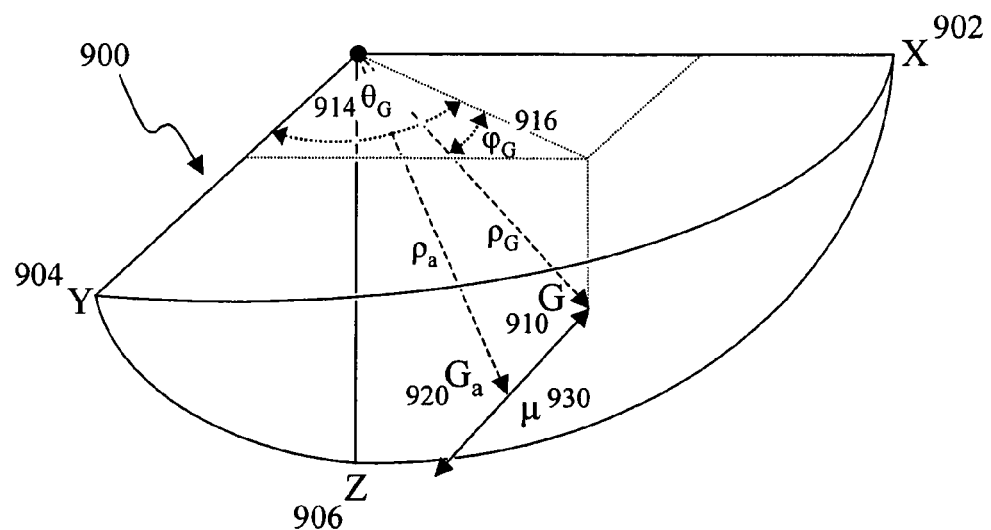
FIG. 9a is a diagram of a geometric model illustrating the operation of the device of FIG. 2a when the device is being subjected to a combined stimulus of tilt and periodic acceleration.

FIG. 9a is a diagram of a geometric model 900 that may be employed to illustrate a technique of distinguishing the effects of acceleration on the orientation and motion-sensing device 210 (see FIGS. 2a-2e) from the effects of tilt. As described above, the accuracy of the measurement of the apparent gravity vector G by the device 210 can decrease in the presence of acceleration, and, in certain applications (such as physical activity monitors), it is useful to estimate the magnitude and direction of the acceleration vector as precisely as possible in order to improve the accuracy of the measurement of physical activity. Like the geometric model 600 of FIG. 6, the geometric model 900 of FIG. 9a is constructed with reference to both the spherical and Cartesian coordinate systems and only one octal portion of the unit sphere is shown. Further, an X-axis 902 represents the sensitive axis of the X-axis sensor 402 (see FIG. 4), a Y-axis 904 represents the sensitive axis of the Y-axis sensor 404 (see FIG. 4), and a Z-axis 906 represents the sensitive axis of the over-range sensor 440. As illustrated in FIG. 9a, an apparent gravity vector G 910 is the sum of an actual gravity vector $G_a$ 920 and an oscillating acceleration vector μ 930, which has its origin at the endpoint of the vector $G_a$ 920, i.e., $$G = G_a + \mu. \quad (11)$$

For example, such an oscillating acceleration vector μ 930 may occur when the user is running and the dominant direction of the acceleration vector μ 930 is up-down relative to the user, or when the user is rowing and the dominant direction of the vector μ 930 is front-back relative to the user.

An illustrative method of distinguishing the effects of acceleration on the device 210 from the effects of tilt is described below with reference to FIGS. 9a, 9b and 10. In this method, it is assumed that the average magnitude of the acceleration vector μ 930 is zero, and that the magnitude variation of the acceleration vector μ 930 is in a higher frequency band than the directional variation of the actual gravity vector $G_a$ 920. As described above, the apparent gravity vector G can be specified in spherical coordinates by angles $\theta_G$ 914 and $\phi_G$ 916.

As depicted in step 1002 (see FIG. 10), signals representing the angles $\theta_G$ 914 and $\phi_G$ 916 (see FIG. 9a) are low-pass filtered by low-pass filter components 940 and 950 (see FIG. 9b), respectively, to suppress just the effects of the acceleration vector μ 930 (see FIG. 9a) from the apparent gravity vector G 910 (see FIG. 9a).

Those of ordinary skill in this art will appreciate that appropriate filter architectures and values 940 and 950 can be chosen to perform this step if the magnitude variation of the acceleration vector μ 930 is in a sufficiently higher frequency band than the directional variation of the actual gravity vector $G_a$ 920. In one exemplary embodiment, a 15-tap, 0.5 Hz FIR filter with a 6 Hz sampling rate will attenuate a periodic acceleration vector μ 930 with a period of 1 second by 33 dB, while attenuating a periodic $G_a$ 920 with a period of 9 seconds by less than 1 dB.

Figure 9B:
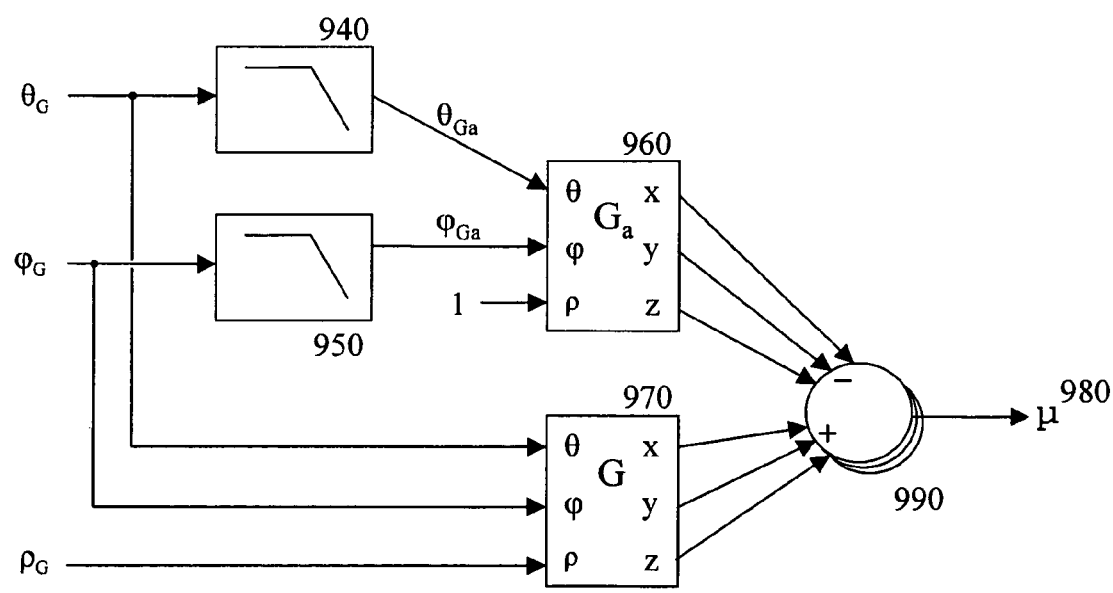

As shown in FIG. 9b, the low pass filters 940 and 950 generate output signals corresponding to angles $\theta_{Ga}$ and $\phi_{Ga}$, respectively, which define the direction of the actual gravity vector $G_a$. Next, assuming that the length $\rho_a$ of $G_a$ is equal to 1 ($\rho_a$=1), signals representing the angles $\theta_{Ga}$ and $\phi_{Ga}$ are converted to Cartesian coordinates by the converter 960 (see FIG. 9b), as depicted in step 1004. Similarly, the signals representing the angles $\theta_G$ 914 and $\phi_G$ 916, and the length $\rho_G$, are converted to Cartesian coordinates by the converter 970 (see FIG. 9b), as depicted in step 1006. Finally, a representation 980 (see FIG. 9b) of the acceleration vector μ 930 is obtained at a summation node 990 (see FIG. 8b) by subtracting the actual gravity vector $G_a$ from the apparent gravity vector G, as depicted in step 1008.

Figure 10:
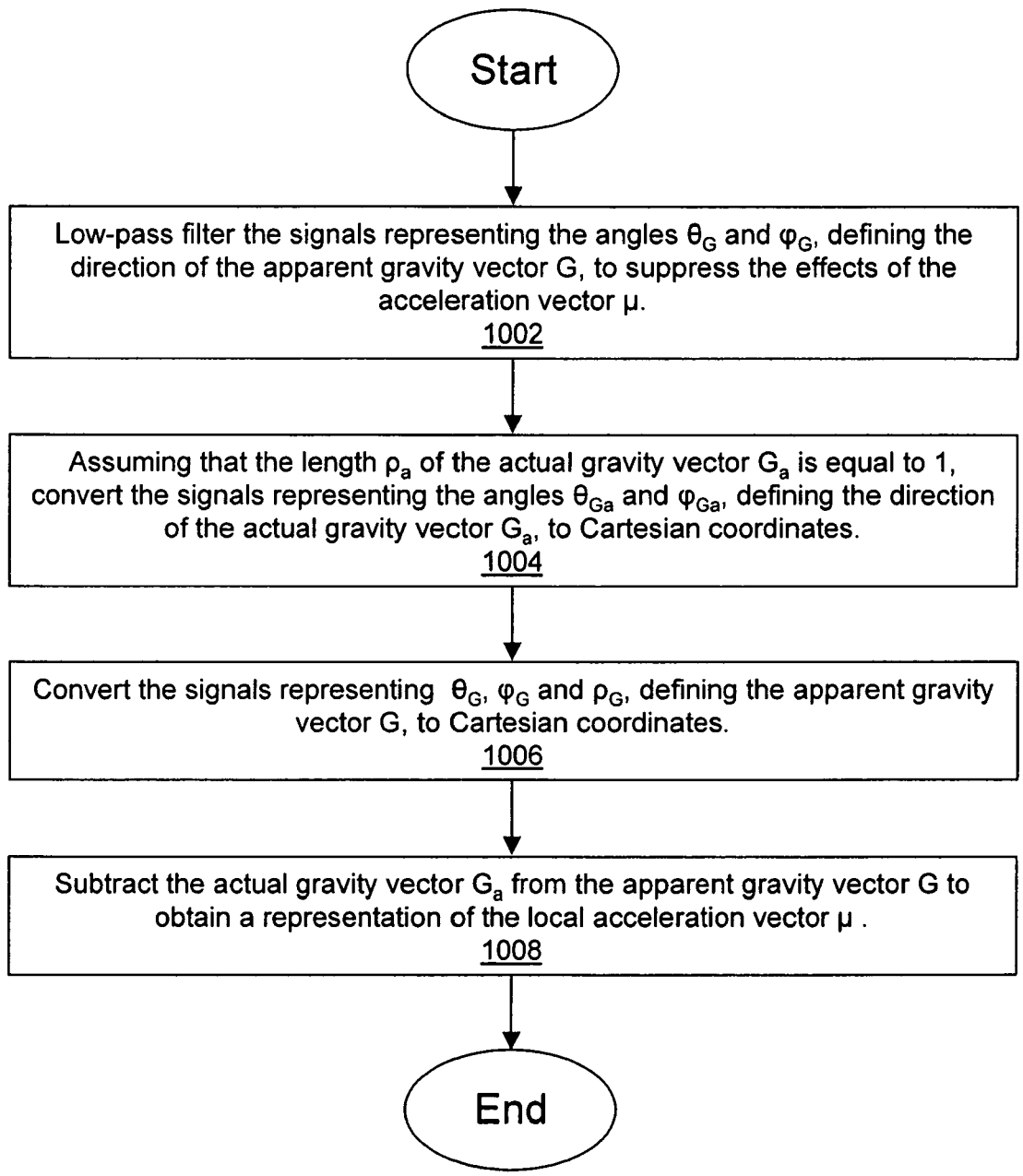
FIG. 10 is a flow diagram of a method of performing the technique of FIG. 9b.

The method of FIG. 10 allows accurate measurements of the direction and magnitude of acceleration of the device 210 to be obtained without having to calibrate the alignment of the device to the user, without knowing a priori the direction of the acceleration relative to the device 210, and without requiring the device's orientation relative to the user to remain constant.

It should be appreciated that the functions necessary to implement the present invention may be embodied in whole or in part using hardware or software or some combination thereof using micro-controllers, microprocessors, digital signal processors, programmable logic arrays, and/or any other suitable hardware and/or software.

It will further be appreciated by those of ordinary skill in this art that modifications to and variations of the above-described systems and methods of monitoring body orientation, posture, and motion, and providing cueing and feedback thereof, may be made without departing from the inventive concepts disclosed herein. Accordingly, the invention should not be viewed as limited except as by the scope and spirit of the appended claims.

What is claimed is:

1. An apparatus for monitoring an orientation of an object in 3-dimensional space, said apparatus being mountable to said object, comprising:
    a 3-axis sensor configured to sense a magnitude of tilt along each of a first axis, a second axis, and a third axis;
    at least one memory operative to store data representative of the sensed magnitude of tilt along each of said first, second, and third axes; and
    at least one processor operative to process the data stored in said at least one memory, wherein said at least one processor is operative:
    to determine an angle between each of said first, second, and third axes and a horizontal plane;
    to select two of said first, second, and third axes corresponding to two smallest angles between said first, second, and third axes and the horizontal plane; and
    to generate an indication of the orientation of said object based upon the sensed magnitude of tilt along the two selected axes.

2. The apparatus of claim 1 wherein said 3-axis sensor includes at least one accelerometer, said 3-axis sensor being operative to measure a magnitude of an apparent gravity force along each of said first, second, and third axes.

3. The apparatus of claim 2 wherein said at least one processor is operative to monitor an acceleration of said object by monitoring the magnitude of said apparent gravity force.

4. The apparatus of claim 2
    wherein said first and second axes are disposed at a first specified angle to one another and define a first plane, said third axis being disposed at a second specified angle to the first plane;
    wherein each of said first and second specified angles is equal to 90°; and
    wherein said at least one processor is operative to determine a direction of said apparent gravity force using at least said first and second axes.

5. The apparatus of claim 2 wherein said at least one processor is operative to detect the presence of an acceleration of said object if the magnitude of said apparent gravity force is not equal to 1.

6. A method of monitoring an orientation of an object in 3-dimensional space, comprising the steps of:
    in a positioning step, positioning a housing including a 3-axis sensor against said object;
    in a sensing step, sensing, by said 3-axis sensor, a magnitude of tilt along a first axis, a second axis, and a third axis; and
    in a determining step, determining an angle between each of said first, second, and third axes and a horizontal plane;
    in a selecting step, selecting two of said first, second, and third axes corresponding to two smallest angles between said first, second, and third axes and the horizontal plane; and
    in a first generating step, generating an indication of the orientation of said object based upon the sensed magnitude of tilt along the two selected axes.

7. The method of claim 6 wherein said sensing step includes measuring, by said 3-axis sensor, a magnitude of an apparent gravity force along each of said first, second, and third axes.

8. The method of claim 7 further including the step of monitoring the magnitude ρ of said apparent gravity force to determine a presence or an absence of an acceleration of said object.

9. The method of claim 7 further including the steps of
    filtering a signal representing a direction of said apparent gravity force to determine a direction of an actual gravity force,
    subtracting a first vector representing said actual gravity force from a second vector representing said apparent gravity force to obtain a third vector, said third vector representing a periodic acceleration of said object, and
    in a second generating step, generating an indication of at least one of a direction and a magnitude of the third vector representing the acceleration of said object.

10. The method of claim 6 further including generating an audible message corresponding to at least one word or phrase at a start or completion of at least one of said positioning step, said sensing step, said determining step, said selecting step, and said first generating step.

11. The method of claim 10 wherein the at least one word or phrase corresponding to said audible message comprises at least one instructional word or phrase.

12. The method of claim 10 wherein the at least one word or phrase corresponding to said audible message comprises a confirmation of the start or completion of a specified act.

13. A method of monitoring an orientation of a body part of a user in 3-dimensional space, comprising the steps of:
    in a positioning step, positioning said body part in a first orientation within the 3-dimensional space;

in a first measuring step, measuring an apparent gravity force acting on said body part at the first orientation to obtain a first direction of said apparent gravity force;

in a first causing step, causing a first angular displacement of said body part about at least one axis from the first orientation to a second orientation within the 3-dimensional space;

in a second measuring step, measuring said apparent gravity force acting on said body part at the second orientation to obtain a second direction of said apparent gravity force;

in a first determining step, determining a reference orientation of said user within the 3-dimensional space based upon the first and second directions of said apparent gravity force acting on said body part at the first and second orientations, respectively; and in a storing step, storing an indication of the reference orientation of said user.

14. The method of claim 13 further including the steps of in a second causing step, causing at least one next angular displacement of said body part about said at least one axis to at least one next orientation within the 3-dimensional space, in a third measuring step, measuring said apparent gravity force acting on said body part at the next orientation to obtain a next direction of said apparent gravity force; and in a second determining step, determining, relative to the reference orientation of said user, a direction corresponding to said next angular displacement based upon the second and next orientations of said body part.

15. The method of claim 13 wherein the reference orientation of said user determined in said first determining step corresponds to a direction along a great circle arc from an end of a first vector representing said apparent gravity force measured in said first measuring step to an end of a second vector representing said apparent gravity force measured in said second measuring step.

16. The method of claim 13 wherein the first angular displacement corresponds to a length of a great circle arc from an end of a first vector representing said apparent gravity force measured in said first measuring step to an end of a second vector representing said apparent gravity force measured in said second measuring step.

17. The method of claim 14 wherein the next angular displacement corresponds to a length of a great circle arc from an end of a first vector representing said apparent gravity force measured in said second measuring step to an end of a second vector representing said apparent gravity force measured in said third measuring step.

18. The method of claim 14 wherein the orientation of said user determined in said second determining step corresponds to a direction along a great circle arc from an end of a first vector representing said apparent gravity force measured in said second measuring step to an end of a second vector representing said apparent gravity force measured in said third measuring step.

19. The method of claim 13 further including generating an audible message corresponding to at least one word or phrase at a start or completion of at least one of said positioning step, said first measuring step, said first causing step, said second measuring step, said first determining step, and said storing step.

20. The method of claim 19 wherein the at least one word or phrase corresponding to said audible message comprises at least one instructional word or phrase.

21. The method of claim 19 wherein the at least one word or phrase corresponding to said audible message comprises a confirmation of the start or completion of a specified act.

22. A method of monitoring a range of motion of a body part, said body part being rotatable about a joint to which said body part is coupled, comprising the steps of:

in a first positioning step, positioning a housing including a sensor against said body part;

in a second positioning step, positioning said body part in a first orientation relative to the joint;

in a first measuring step, measuring, by said sensor in 3-dimensional space, an apparent gravity force acting on said housing disposed against said body part at the first orientation to obtain a first direction of said apparent gravity force;

in a third positioning step, positioning said body part in a second orientation relative to the joint;

in a second measuring step, measuring, by said sensor in 3-dimensional space, said apparent gravity force acting on said housing disposed against said body part at the second orientation to obtain a second direction of said apparent gravity force;

in a determining step, determining a magnitude of rotation of said body part from the first orientation to the second orientation based upon the first and second directions of said apparent gravity force; and in a providing step, providing an indication of the magnitude of rotation of said body part.

23. The method of claim 22 wherein said first positioning step includes positioning said housing including said sensor against said body part, wherein said sensor has at least two axes.

24. The method of claim 22 wherein the magnitude of rotation of said body part corresponds to a length of a great circle arc from an end of a first vector representing said apparent gravity force measured in said first measuring step to an end of a second vector representing said apparent gravity force measured in said second measuring step.

25. The method of claim 22 wherein said second measuring step includes performing a plurality of measurements of said apparent gravity force at substantially the second orientation to obtain a plurality of second directions of said apparent gravity force, wherein the determining step includes determining a plurality of magnitudes of rotation of said body part from the first orientation to substantially the second orientation based upon the first direction and the plurality of second directions of said apparent gravity force, and further including storing a maximum of the plurality of magnitudes of rotation.

26. The method of claim 22 further including generating an audible message corresponding to at least one word or phrase at a start or completion of at least one of said first positioning step, said second positioning step, said first measuring step, said third positioning step, said second measuring step, said determining step, and said providing step.

27. The method of claim 26 wherein the at least one word or phrase corresponding to said audible message comprises at least one instructional word or phrase.

28. The method of claim 26 wherein the at least one word or phrase corresponding to said audible message comprises a confirmation of the start or completion of a specified act.

29. A method of initiating monitoring of an orientation of a body part in 3-dimensional space, said monitoring being performed using a sensor disposed against said body part, comprising the steps of:

in a first positioning step, positioning said body part in a first orientation within the 3-dimensional space;

in a first providing step, providing, by said sensor, data representing a first position of said body part at the first orientation;

in a second positioning step, positioning said body part in at least one second orientation within the 3-dimensional space;

in a second providing step, providing, by said sensor, data representing at least one second position of said body part at the at least one second orientation; and in an initiating step, in the event the first position of said body part at the first orientation and the at least one second position of said body part at the at least one second orientation correspond to a specified sequence of positions of said body part, initiating said monitoring of the orientation of said body part by said sensor.

30. The method of claim 29 wherein the first providing step includes measuring, by said sensor, an apparent gravity force acting on said body part at the first orientation to obtain a first direction of said apparent gravity force, the first direction of said apparent gravity force being indicative of the first position of said body part at the first orientation, and wherein the second providing step includes measuring, by said sensor, said apparent gravity force acting on said body part at the at least one second orientation to obtain at least one second direction of said apparent gravity force, wherein the at least one second direction of said apparent gravity force is indicative of the at least one second position of said body part at the at least one second orientation.

31. The method of claim 29 further including generating an audible message corresponding to at least one word or phrase at a start or completion of at least one of said first positioning step, said first providing step, said second positioning step, said second providing step, and said initiating step.

32. The method of claim 31 wherein the at least one word or phrase corresponding to said audible message comprises at least one instructional word or phrase.

33. The method of claim 31 wherein the at least one word or phrase corresponding to said audible message comprises a confirmation of the start or completion of a specified act.

34. An apparatus for monitoring an orientation of a body part, the apparatus being attachable to said body part, comprising:

a sensor operative to sense at least one angular orientation of said body part, and to provide data representing the at least one sensed angular orientation;

at least one memory operative to store data representing a plurality of words or phrases;

an audio output system operative to generate an audible message in response to an electronic input; and at least one processor operative;

to monitor the data provided by said sensor;

to generate, based upon the data provided by said sensor, at least one quantitative value corresponding to the at least one sensed angular orientation of said body part;

to access data stored in said memory corresponding to at least one word or phrase, said at least one word or phrase relating to said at least one quantitative value corresponding to the at least one sensed angular orientation of said body part; and to generate, in cooperation with said audio output system, an audible message corresponding to said at least one word or phrase.

35. The apparatus of claim 34 wherein the at least one word or phrase corresponding to said audible message comprises at least one instructional word or phrase.

36. The apparatus of claim 34 wherein the at least one word or phrase corresponding to said audible message comprises a confirmation of a start or completion of a specified act.

37. The apparatus of claim 34 wherein the at least one word or phrase corresponding to said audible message comprises a representation of a voice of one of a plurality of predetermined individuals.

38. The apparatus of claim 37 wherein one of said plurality of predetermined individuals is selectable by a user.

39. The apparatus of claim 34 wherein the data representing said plurality of words or phrases is stored in said memory in a plurality of different languages.

40. The apparatus of claim 39 wherein one of said plurality of different languages is selectable by a user.

41. The apparatus of claim 34 wherein said at least one processor is communicably coupleable to a data communications network.

42. The apparatus of claim 41 wherein said data communications network comprises one of a local area network (LAN), a wide area network (WAN), and a point-to-point network/remote-control unit.

43. The apparatus of claim 41 wherein sat at least one processor is operative to receive data corresponding to said plurality of words or phrases over said network, and to store said data in said memory.

44. The apparatus of claim 34 further including an interface configured to communicate information over a data communications network, and wherein said at least one processor is operative to store said data provided by said sensor, to generate at least one data message containing said data provided by said sensor, and to communicate said data message to said interface for subsequent transmittal over said network.

45. An apparatus for monitoring an orientation of a body part of a user, the apparatus being attachable to said body part, comprising:

a sensor configured to sense an angular orientation of said body part, and to provide data representing the sensed angular orientation;

a memory operative to store data representative of a plurality of indications of the sensed angular orientation of said body part;

an output system operative to generate a plurality of indications perceptible by the user; and at least one processor operative;

to monitor data provided by said sensor; and to access data corresponding to at least one of said plurality of indications of the sensed angular orientation of said body part, and, in cooperation with said output system, to generate one of said indications perceptible by the user to provide the user with feedback pertaining to the orientation of said body part within the 3-dimensional space, wherein said output system comprises at least one vibrating transducer, and said indications perceptible by the user comprise a plurality of predetermined vibration patterns.

* * * * *

UNITED STATES PATENT AND TRADEMARK OFFICE
CERTIFICATE OF CORRECTION

PATENT NO. : 7,383,728 B2
APPLICATION NO. : 11/485180
DATED : June 10, 2008
INVENTOR(S) : Christopher R. Noble et al.

It is certified that error appears in the above-identified patent and that said Letters Patent is hereby corrected as shown below:

Column 9, line 9, "apparatus" should read --apparent--;

Column 10, line 31, "530" should read --520--;

Column 12, Equation 2, lines 63-64:
"$\cos \psi_{12} = (\sin \phi_1 * \sin \phi_2) + (\cos (\theta_2 - \theta_1) * \cos \phi_1 * \cos \phi_2)$  (2)"
should read
--$\cos \psi_{12} = (\sin \varphi_1 * \sin \varphi_2) + (\cos (\theta_2 - \theta_1) * \cos \varphi_1 * \cos \varphi_2)$  (2)--;

Column 13, Equation 3, line 5:
"$\cos \eta_{21} = (\sin \phi_1 - (\sin \phi_2 * \cos \psi_{12}))/(\cos \phi_2 * \sin \psi_{12})$  (3)"
should read
--$\cos \eta_{21} = (\sin \varphi_1 - (\sin \varphi_2 * \cos \psi_{12}))/(\cos \varphi_2 * \sin \psi_{12})$  (3)--;

Column 13, Equation 4, line 18:
"$\cos \eta_{2n} = (\sin \phi_n - (\sin \phi_2 * \cos \psi_{n2}))/(\cos \phi_2 * \sin \psi_{n2})$  (4)"
should read
--$\cos \eta_{2n} = (\sin \varphi_n - (\sin \varphi_2 * \cos \psi_{n2}))/(\cos \varphi_2 * \sin \psi_{n2})$  (4)--;

Column 13, Equation 9, lines 34-35:
"$\cos \psi_{2n} = (\sin \phi_2 * \sin \phi_n) + (\cos (\theta_n - \theta_2) * \cos \phi_2 * \cos \phi_n)$,  (9)"
should read
--$\cos \psi_{2n} = (\sin \varphi_2 * \sin \varphi_n) + (\cos (\theta_n - \theta_2) * \cos \varphi_2 * \cos \varphi_n)$,  (9)--;

Column 14, Equation 10, lines 1-2:
"$\cos \psi_{1n} = (\sin \phi_1 * \sin \phi_n) + (\cos (\theta_n - \theta_1) * \cos \phi_1 * \cos \phi_n)$.  (10)"
should read
--$\cos \psi_{1n} = (\sin \varphi_1 * \sin \varphi_n) + (\cos (\theta_n - \theta_1) * \cos \varphi_1 * \cos \varphi_n)$.  (10)--;

UNITED STATES PATENT AND TRADEMARK OFFICE
CERTIFICATE OF CORRECTION

PATENT NO. : 7,383,728 B2
APPLICATION NO. : 11/485180
DATED : June 10, 2008
INVENTOR(S) : Christopher R. Noble et al.

It is certified that error appears in the above-identified patent and that said Letters Patent is hereby corrected as shown below:

Column 16, line 54, "ɸ" should read --φ--;

Column 16, line 56, "ɸ" should read --φ--;

Column 17, line 5, "ɸ" should read --φ--;

Column 17, line 8, "ɸ" should read --φ--;

Column 17, line 11, "ɸ" should read --φ--;

Column 17, line 15, "8b" should read --9b--; and

Column 22, claim 43, line 26, "sat" should read --said--.

Signed and Sealed this

Fifteenth Day of September, 2009

David J. Kappos
*Director of the United States Patent and Trademark Office*